United States Patent [19]

Burba, III et al.

[11] Patent Number: 5,481,042
[45] Date of Patent: Jan. 2, 1996

[54] PROCESSES PRODUCING METHYL MERCAPTAN

[75] Inventors: John L. Burba, III; James T. Ayres; Preston E. Spires, all of El Dorado, Ark.; John E. Hill, West Lafayette, Ind.

[73] Assignee: Great Lakes Chemical Corp., West Lafayette, Ind.

[21] Appl. No.: 225,592

[22] Filed: Apr. 11, 1994

[51] Int. Cl.$^6$ ............................................. C07C 319/02
[52] U.S. Cl. ................................................. 568/70
[58] Field of Search ............................... 568/70

[56] References Cited

U.S. PATENT DOCUMENTS

| 2,147,400 | 2/1939 | Clark et al. | 568/70 |
| 2,404,425 | 7/1946 | Beanblossom et al. | 568/70 |
| 2,816,145 | 12/1957 | Ch'in et al. | 568/70 |
| 4,740,623 | 4/1988 | Heather | 568/68 |

FOREIGN PATENT DOCUMENTS

| 2049753 | 3/1992 | Canada | 568/70 |
| 956469 | 9/1982 | U.S.S.R. | 568/70 |

*Primary Examiner*—James H. Reamer
*Attorney, Agent, or Firm*—Woodard, Emhardt, Naughton Moriarty & McNett

[57] ABSTRACT

Described are preferred processes which produce methyl mercaptan from methyl bromide and aqueous mediums of metal hydrosulfide. The processes can be used to simultaneously consume methyl bromide byproduct and aqueous NaSH byproduct while producing methyl mercaptan.

25 Claims, 3 Drawing Sheets

PROCESSES PRODUCING METHYL MERCAPTAN

BACKGROUND OF THE INVENTION

The present invention relates generally to the production of methyl mercaptan. More particularly, the invention relates processes producing methyl mercaptan by the reaction of methyl bromide with sodium hydrosulfide, and which can be implemented to convert both sodium hydrosulfide and methyl bromide byproducts to the more desirable methyl mercaptan.

As further background, two very significant problems that face bromine ($Br_2$) producers and utilizers involve hydrogen sulfide ($H_2S$) and methyl bromide ($CH_3Br$). The $H_2S$ problem is the result of bromine recovery. Geothermal brine formations, for example those occurring in the Southern United States, are a rich source of bromine. Several $Br_2$ producing companies "mine" this brine with wells. To produce $Br_2$, bromide ions in the brine are oxidized with $Cl_2$ and $Br_2$ is recovered. Unfortunately, brine from geothermal formations can also contain significant quantities of $H_2S$, which must be stripped from the brine. $H_2S$ cannot be burned or released into the atmosphere without posing safety or environmental concerns and has thus been regulated in a number of countries Therefore, $H_2S$ has traditionally been absorbed in NaOH to form sodium hydrosulfide (NaSH).

Until recently, NaSH was utilized in large quantities by the paper industry. However, a combination of industry-specific changes and tightening of sulfur emission rules by regulatory agencies such as the Environmental Protection Agency (EPA) in the U.S. have produced a significant glut in the NaSH market. One alternative is to produce sulfur; however, difficulties are also encountered in attempting to find a market outlet for sulfur.

A second obstacle, encountered in the flame retardant industry, relates to the production of substantial quantities of methyl bromide ($CH_3Br$) in the manufacture of certain brominated flame retardants such as tetrabromobisphenol A. Methyl bromide is another material identified as posing health and safety concerns, and is the subject of regulation by agencies such as the EPA in the U.S. The obvious impact is the potential curtailment of critical flame retardant production.

Faced with these challenges there are critical needs in the bromine and flame retardant industries for means of ameliorating the limitations posed by NaSH and methyl bromide byproducts. The present invention addresses these needs.

SUMMARY OF THE INVENTION

One object of the present invention is to provide a process for converting byproduct sodium hydrosulfide from a geothermal brine operation to a more valuable product, methyl mercaptan.

Another object of the invention is to provide a process for converting byproduct methyl bromide from a flame retardant manufacture to methyl mercaptan.

Another object of the invention is to provide a process which consumes both byproducts, sodium hydrosulfide and methyl bromide, with the formation of methyl mercaptan.

These and other objects are attained by the invention, one preferred embodiment of which provides a process for producing methyl mercaptan which includes stripping a geothermal brine containing bromide ions and hydrogen sulfide to remove the hydrogen sulfide as a gas. The hydrogen sulfide gas is contacted with an aqueous medium containing an alkali or alkaline earth metal hydroxide to form an aqueous medium containing an alkali or alkaline earth metal hydrosulfide. The aqueous medium containing the alkali or alkaline earth metal hydrosulfide is contacted and reacted with methyl bromide in a reactor so as to form methyl mercaptan, and the methyl mercaptan so formed is recovered from the reactor.

Another preferred embodiment of the invention provides a process for producing methyl mercaptan, which includes providing a reactor containing solid materials providing surface area for interaction among gas and liquid phases within the reactor. Methyl bromide, in gaseous form, is fed into the reactor where it is intimately contacted with an aqueous solution of sodium hydrosulfide. The high surface area solid materials within the reactor promote interaction among the gaseous methyl bromide and aqueous sodium hydrosulfide, which react to form methyl mercaptan. The formed methyl mercaptan can then be recovered from the reactor.

Still another preferred embodiment of the invention provides a pressurized process for producing methyl mercaptan, which includes continuously feeding methyl bromide through a pressurized, mixed reactor at a pressure sufficiently high to substantially maintain the methyl bromide in a liquid state. An aqueous sodium hydrosulfide solution is fed through the reactor simultaneously with the liquid methyl bromide, wherein the mixed reactor mixes and reacts the methyl bromide and aqueous sodium hydrosulfide to form methyl mercaptan. The methyl mercaptan can then be recovered from the reactor.

The invention thus provides processes which consume potentially problematic byproducts while producing methyl mercaptan which is a valuable intermediate to other products, including inter alia methionine.

Additional embodiments, as well as features and advantages of the invention, will be apparent from the following description.

DESCRIPTION OF THE PREFERRED EMBODIMENT

Figure 1:
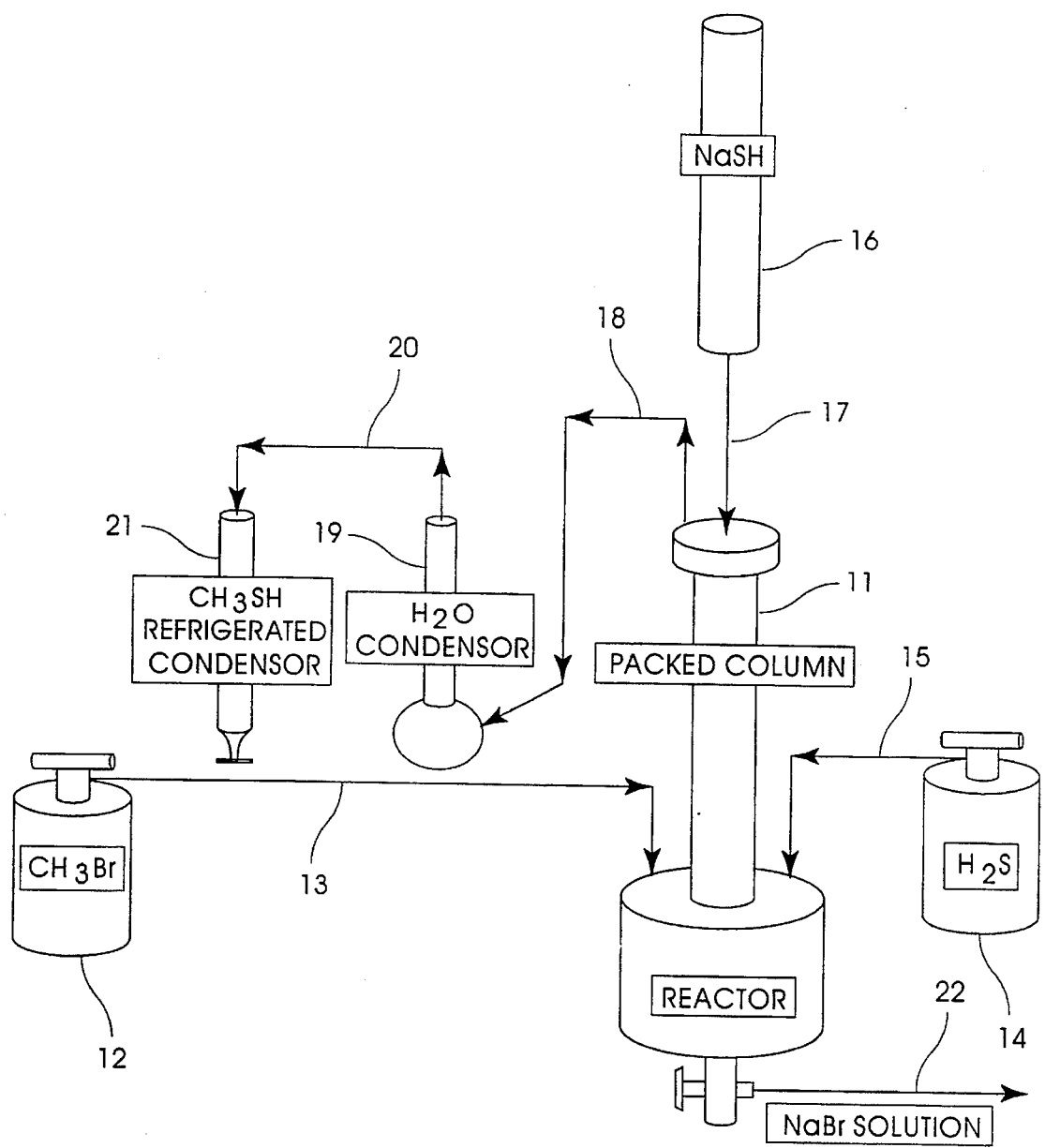
FIG. 1 provides a schematic diagram illustrating a preferred methyl mercaptan process of the invention conducted in a packed column reactor.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications, and applications of the principles of the invention as illustrated herein being contemplated as would normally occur to one skilled in the art to which the invention pertains.

As indicated above, the present invention provides methods which can be used to convert methyl bromide and an alkali or alkaline earth metal hydrosulfide to methyl mercaptan. These methods can be capitalized upon in both the brine mining and fire retardant industries.

In the brine mining industries, brine is conventionally treated so as to remove hydrogen sulfide as a gas. The hydrogen sulfide is then typically reacted with an alkali metal hydroxide such as sodium hydroxide to form an alkali metal hydrosulfide, although alkaline earth metal hydroxides such as calcium hydroxide can also be used. Presently, there is not sufficient demand for the produced metal hydrosulfide to consume supply, and thus there is a need for methods for converting the metal hydrosulfide to other valuable materials for which a greater market exists.

In the fire retardant industry, many brominations of aromatic substrates are carried out in methanol, resulting in methyl bromide as a byproduct. Methyl bromide also lacks sufficient commercial outlets to consume amounts produced as byproduct and its production is being curtailed for safety and environmental reasons. In accordance with the present invention, this methyl bromide can be consumed with the production of methyl mercaptan, thus alleviating disposal problems and the attendant costs. Advantageously, processes of the present invention can be used in facilities with which both mine brine and produce flame retardants by bromination of organic substrates in a solvent system including methanol, with methyl bromide byproduct formation. In such facilities, the byproduct methyl bromide and the byproducts metal hydrosulfide can be advantageously reacted to consume both while forming valuable methyl mercaptan.

More particularly describing aspects of the invention, as specifically applied to the consumption of NaSH, the starting aqueous NaSH medium will typically be comprised about 10 to about 30 percent by weight of NaSH, more typically about 15 to about 30 percent by weight. When the NaSH source is produced by the removal of hydrogen sulfide from brine and reaction of that hydrogen sulfide with sodium hydroxide, the NaSH solution will typically contain other impurities including, for example, sodium bicarbonate ($Na_2CO_3$), sodium sulfide ($Na_2S$), and chloride ion ($Cl^-$). Typically, sodium bicarbonate is present as an impurity in an amount ranging from about 1 percent to about 5 percent, sodium sulfide is present in an amount of about 1 percent to about 5 percent, and chloride ion is present in amounts up to about 3000 mg/kg or more of NaSH solution. Aqueous NaSH byproduct from brine processing can be used as is or optionally can be diluted prior to reaction with the methyl bromide, for example, to ameliorate problems associated with the precipitation of sodium bicarbonate, which might foul or cause plugging in the reactor. Alternatively, aqueous NaSH solutions, for example having starting pH's in the range of about 10 to about 11, can be acidified using mineral acid or $H_2S$ in order to precipitate sodium bicarbonate, which can then be separated by filtration or other conventional means. Such acidifications are preferably sufficient to reduce the sodium bicarbonate level of the NaSH solution to less than about 1%. In the applicants' experience, acidification to a pH in the range of about 8 to 8.5 has been sufficient for these purposes.

Additionally, the sodium or other metal hydrosulfide can be produced in situ by feeding the $H_2S$ stripped from the brine directly to the reactor along with an aqueous medium containing the appropriate metal hydroxide. In this case, the $H_2S$ feed can also be enriched in $H_2S$ and reduced in its carbon dioxide ($CO_2$) content prior to feed to the reactor to avoid potential solids problems. This enrichment can be achieved using known means, for example by treatment of the $H_2S$ stream with an amine-containing medium which selectively absorbs the $H_2S$, and subsequent liberation of the $H_2S$ to form a purified $H_2S$ stream.

The methyl bromide used in the present invention can be, for example, the byproduct from the reaction of an organic substrate, such as an aromatic substrate, with a brominating agent in methanol to produce a fire retardant material such as tetrabromobisphenol A. A byproduct stream from such reaction will usually include methyl bromide and typically also other impurities such as methyl ether ($CH_3OCH_3$), methyl chloride ($CH_3Cl$), and methanol ($CH_3OH$). These impurities are usually present in small amounts, for example less than 0.1 percent by weight.

In accordance with the invention, the aqueous NaSH solution and the methyl bromide will be contacted in a manner which promotes reaction to form methyl mercaptan quickly and efficiently. It has been discovered that the reaction of aqueous NaSH and methyl bromide proceeds rapidly and can be used to effectively form methyl mercaptan in very high yield. For example, yields of greater than about 70% and even approaching 100% can be readily obtained in accordance with the present invention.

Reactions of the present invention will be conducted at a temperature sufficiently high to promote the reaction of the methyl bromide and sodium hydrosulfide. For example, reactions of the invention are suitably conducted at temperatures in the range of about 20° C. to about 150° C., more preferably in the range of about 20° C. to about 100° C. Similarly, processes of the invention can be conducted over a broad range of pressures. Preferred pressures range from about ambient pressure up to about 1000 or more psig, more preferably from about ambient up to about 300 psig.

Preferred processes of the invention will employ at least an equimolar amount of NaSH relative to methyl bromide, more preferably a slight molar excess of NaSH relative to methyl bromide. In advantageous processes the NaSH:methyl bromide molar ratio will thus be about 1:1 to 2:1, more preferably about 1.1:1 to about 1.2:1.

To improve selectivity for methyl mercaptan and to minimize the formation of byproducts, it is also preferred to react the aqueous sodium hydrosulfide and the methyl bromide in the presence of added hydrogen sulfide. It has been found that the addition of hydrogen sulfide significantly reduces production of the byproduct methyl sulfide ($CH_3SCH_3$) and significantly increases selectivity for methyl mercaptan. Thus, preferred reactions of the present invention will be conducted in the presence of hydrogen sulfide, preferably in amounts sufficient to achieve a hydrogen sulfide:methyl bromide molar ratio of up to about 0.5:1. In accordance with the invention, the use of hydrogen sulfide in these amounts has been sufficient to maintain dimethyl sulfide levels in the product below about 1%.

Processes of the present invention are preferably conducted in a continuous fashion. Representative continuous processes can be conducted using gas/liquid or liquid/liquid contacting apparatuses. For example, gas/liquid processes can be conducted in packed column reactors in which methyl bromide vapors are contacted with the aqueous sodium hydrosulfide, as illustrated in FIG. 1. Liquid/liquid processes can be conducted in pressurized continuous reactors in which liquid methyl bromide is contacted with aqueous sodium hydrosulfide and vigorously mixed or agitated to promote the reaction of the starting materials to produce methyl mercaptan, as illustrated in FIG. 2.

Referring now more particularly to FIG. 1, shown is a schematic diagram of a packed column reactor and process which can be used in accordance with the invention to produce methyl mercaptan. A packed column reactor 11 is provided containing materials providing a high surface area to promote contact of liquid and gas phases. The material can any one of those conventionally utilized for such purposes, for example ceramic saddles, distillation trays, or dimensionally stabilized packing constructed of ceramic or the like. Methyl bromide, for instance that occurring as a byproduct from a bromination in methanol, is fed to the bottom of reactor 11 from pressurized feed tank 12 via line 13. $H_2S$ is also fed to the bottom of reactor 11, from pressurized feed tank 14 via line 15. An aqueous NaSH solution is fed into the top of packed column reactor 11 from feed tank 16 via line 17. In this manner, aqueous NaSH solution and the methyl bromide/$H_2S$ gases are processed countercurrent through packed column reactor 11 which provides a high surface area for interaction among the gas and liquid phases to promote the formation of methyl mercaptan. The methyl mercaptan product is recovered as a gas via line 18 at the top of packed column reactor 11. Product in line 18 is preferably fed into water condenser 19 ho remove unwanted vapors, and the methyl mercaptan is recovered overhead and fed via line 20 to refrigerated condenser 21. Aqueous sodium bromide is collected from the bottom of reactor 11 via line 22 and can, for instance, be used conventionally in the production of bromine or in water treatment applications.

As demonstrated in Example 4 below, gaseous methyl bromide and aqueous NaSH solutions can be effectively reacted in such packed column reactors to rapidly produce methyl mercaptan in high yield. In particular, yields of 50% or greater, for example 70%, can readily be obtained. Any unreacted methyl bromide and $H_2S$ can be recycled back through reactor 11 if desired.

Figure 2:
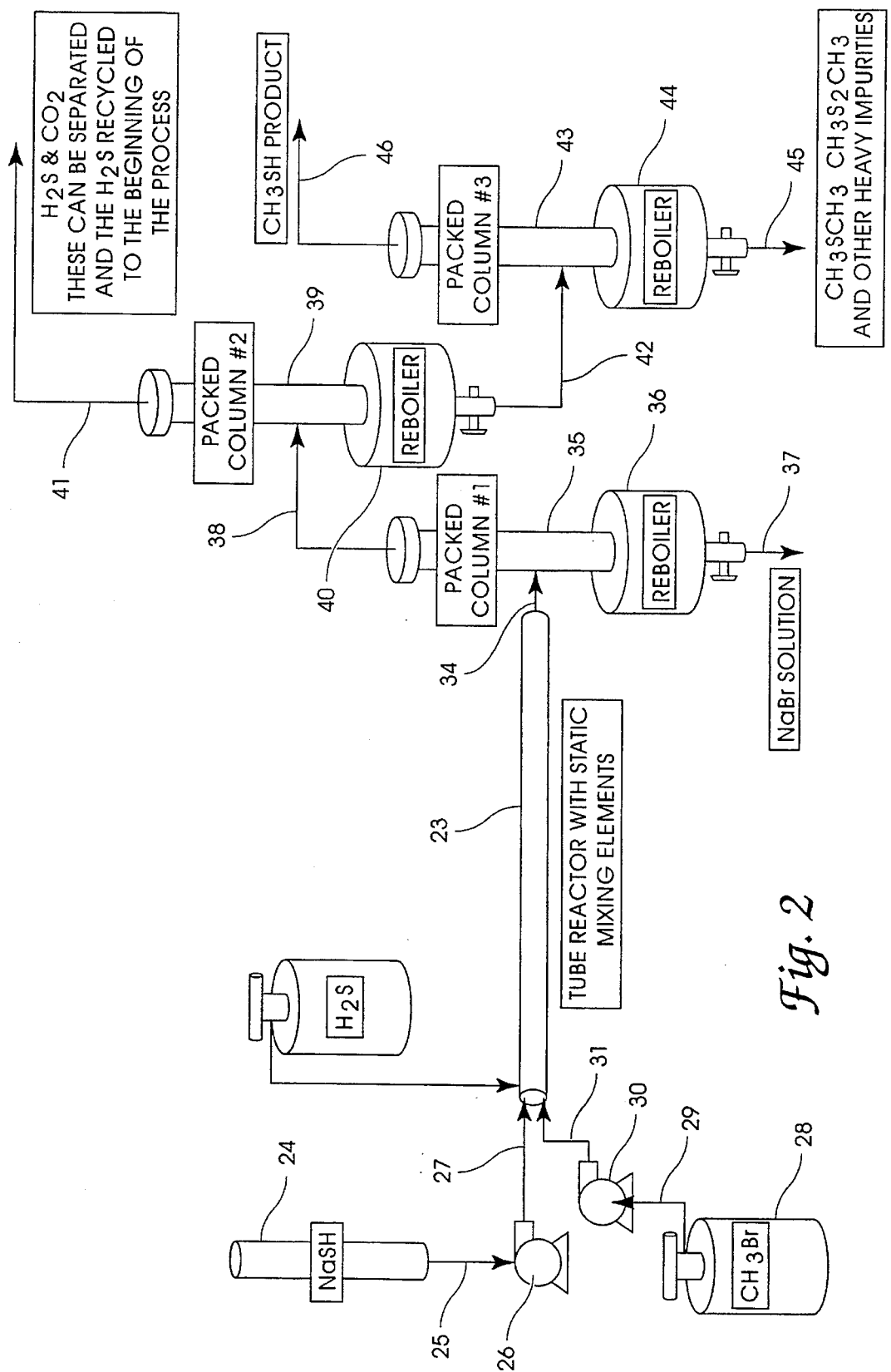
FIG. 2 provides a schematic diagram illustrating a preferred methyl mercaptan process of the invention conducted in a mixed, continuous tube reactor.

Referring now to FIG. 2, shown is a schematic diagram illustrating a pressurized continuous tube reactor and reaction scheme which can be used to carry out processes of the present invention. A tube reactor 23 is provided containing a plurality of static mixing elements which thoroughly admix liquid reactants continuously passed through reactor 23. An aqueous NaSH solution is fed from feed tank 24 via line 25 into positive displacement pump 26. NaSH output from pump 26 is continuously fed via line 27 ho reactor 23. A pressurized methyl bromide feed tank 28 feeds methyl bromide to positive displacement pump 30 via line 29. The methyl bromide output from pump 30 is continuously fed through line 31 into reactor 23. Pumps 26 and 30 effectively create a pressure in reactor 23 which substantially maintains the methyl bromide (and $H_2S$) in a liquid state, generally ranging above about 50 psig and more preferably in the range of about 100 to about 300 psig. $H_2S$ is continuously fed from pressurized tank 32 via line 33 into reactor 23. Within reactor 23, static mixing elements vigorously admix the reactants and promote the rapid formation of methyl mercaptan. The static mixing elements can be blades, torroidal sections, or other physical shapes which promote mixing. Additionally, it will be understood that mechanized mixing elements could also be used to admix the reactants, and their use is contemplated as being within the spirit and scope of the present invention.

Crude product from reactor 23 is then subjected to a series of separations to recover the methyl mercaptan product. Particularly, the reactor output is fed via line 34 to a first packed column separator 35 coupled to reboiler 36. Aqueous sodium bromide is collected from reboiler 36 via line 37 and can, if desired, be conventionally used in the production of bromine. Overhead gases from column 35 are fed via line 38 into second packed column 39, maintained at a temperature which removes $H_2S$ and $CO_2$ as gases overhead via line 41. Product from reboiler 40 is fed via line 42 into a third packed column separator 43 coupled to reboiler 44. This separation unit is maintained at temperatures effective to recover methyl mercaptan as a gas via line 46 and remove byproducts such as methyl sulfide from reboiler 44 via line 45. Example 5 below demonstrates that highly effective conversions of aqueous NaSH and methyl bromide to methyl mercaptan are obtained by such a pressurized, liquid/liquid process, with conversions to methyl mercaptan ranging from 70% up to nearly 100%.

Figure 3:
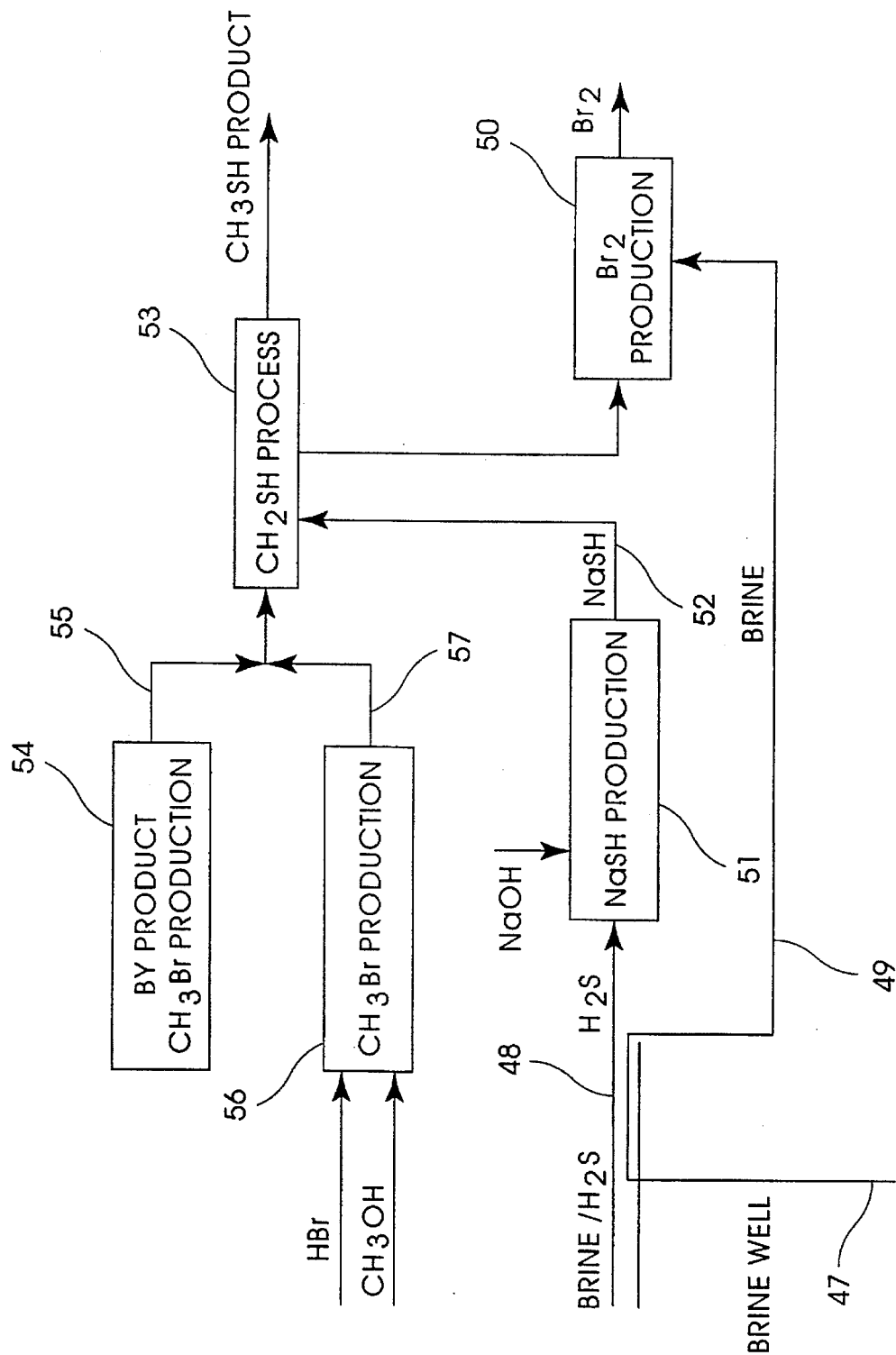
FIG. 3 provides a schematic diagram illustrating a preferred, integrated process of the invention in which byproduct methyl bromide from a flame retardant manufacture and byproduct sodium hydrosulfide from a brine treatment are simultaneously consumed with the formation of methyl mercaptan.

Referring now to FIG. 3, shown is a schematic diagram illustrating a methyl mercaptan process integrated into a flame retardant production having a methyl bromide byproduct stream and a brine processing operation producing aqueous NaSH as a byproduct. An $H_2S$-containing sodium bromide brine is recovered from brine well 47 by conventional operations. The brine is stripped to remove $H_2S$ 48, and the brine 49 is then fed into $Br_2$ production unit 50 and conventionally converted to $Br_2$, for example using $Cl_2$ to convert bromide ions to $Br_2$. $H_2S$ 48 is absorbed in aqueous NaOH in unit 51 to produce aqueous NaSH 52. NaSH 52 is then fed into methyl mercaptan production unit 53, for example incorporating a reaction process as in FIGS. 1 or 2. Unit 54 produces byproduct methyl bromide, for example from the bromination of bisphenol A in methanol to produce tetrabromobisphenol A. Byproduct methyl bromide 55 is also fed into methyl mercaptan production unit 53 to be reacted with NaSH 52 to produce methyl mercaptan. Optionally, additional methyl bromide 57 can be produced in unit 56 by the reaction of HBr and methanol, and fed to methyl mercaptan production unit 53. Unit 56 might be used, for example, if byproduct methyl bromide 55 is not sufficient in quantity to consume all of the NaSH 52 produced in the brine operation. In this fashion, two potentially problematic byproducts, methyl bromide and NaSH, are consumed in an integrated process to produce the more valuable product, methyl mercaptan.

Reactors and other system components used in the invention can be constructed of standard materials such as metals, ceramics, glass or plastics. Preferably, reactor and other system components contacting sodium bromide solutions will be constructed of materials which resist attack by such solutions. For example, components made of or coated with materials such as teflon or glass, or made of corrosion-resistant metals such as high nickel alloys (e.g. Hastelloy), are preferred where contact with sodium bromide solutions is anticipated. Other components which are not to contact sodium bromide solutions can be made of conventional materials, for example stainless steel.

For the purposes of promoting a further understanding of the invention and appreciation of its features and advantages, the following specific Examples are provided. It will be understood that these Examples are illustrative and not limiting in nature.

EXAMPLE 1

Reaction of $Ch_3Br$ and NaSH to Produce $CH_3SH$

This Example was conducted using the following equipment, conditions and starting materials:
Apparatus: 100 ml Septum Vial Magnetic Stirring Bar
Conditions: Initial temperature=25° C.

Reactants: 47.1 g NaSH solution; 23.7 g $CH_3Br$

| Raw Material Analysis | | | |
|---|---|---|---|
| NaSH | | $CH_3Br$ | |
| $Na_2CO_3$ | 4.15% | $CH_3OCH_3$ | 0.065% |
| $Na_2S$ | 3.72% | $CH_3Cl$ | 0.008% |
| NaSH | 20.20% | $CH_3OH$ | 5 ppm |
| Cl | 2,580 mg/Kg | | |

NaSH and $CH_3Br$ in the quantities listed above, were injected into a 100 ml septum vial containing a magnetic stirring bar. Initially, two phases were visible. There was no evidence of reaction until stirring was begun. At this time, an immediate exotherm was observed. This was followed by a phase inversion and the development of copious quantities of precipitate. The total time allowed for reaction was about 4 hours. The vial was allowed to cool and the organic phase was vented into a gas bag. The liquid phase was diluted, acidified with HBr, and boiled. The resultant liquid was found to be an aqueous solution of NaBr, essentially free of NaSH. It was also essentially odor free. The gas sample was analyzed by Gas Chromatograph/Mass Spectrometry (GM/MS), using a Hewlett Packard 5890 Series II Gas Chromatograph coupled to a Hewlett Packard 5971A MSD. The results are set forth in Table 1 below.

TABLE 1

| Compound | GC/MS Analysis (Calculated on Basis of Area) |
|---|---|
| $H_2S$ | 2.3% |
| $CH_3OCH_3$ | 0.4% |
| $CH_3SH$ | 54.8% |
| $CH_3Br$ | 25.0% |
| $CH_3SCH_3$ | 16.0% |
| $CH_3S_2CH_3$ | 0.1% |

EXAMPLE 2

The following equipment, conditions and starting materials were used in this Example.
Apparatus: 1000 ml sealed bottle
Conditions: Initial temperature=25° C.
Reactants: 704.3 g NaSH solution; 234.0 g $CH_3Br$

| Raw Material Analysis | | | |
|---|---|---|---|
| NaSH | | $CH_3Br$ | |
| $Na_2CO_3$ | 4.15% | $CH_3OCH_3$ | 0.065% |
| $Na_2S$ | 3.72% | $CH_3Cl$ | 0.008% |
| NaSH | 20.20% | $CH_3OH$ | 5 ppm |
| Cl | 2,580 mg/Kg | | |

Raw materials were charged into the bottle at about 25° C. Agitation was begun with an internal magnetic stirring bar. Phase inversion and NaBr precipitate were observed. The reaction ran for 4 hours. The reaction was then cooled, and vapors were vented into a gas bag. The liquid phase was acidified with 48% HBr and boiled. It was then cooled for 12 hours and neutralized with NaOH and dried. The NaBr powder from an initial run had a small mercaptan odor. Another drying experiment was conducted in which a small amount of $Br_2$ was added prior to drying. The resultant dry salt was essentially odor-free.

TABLE 2

| NaBr Analysis | |
|---|---|
| Assay | 97.2% |
| Turbidity | 6.3 |
| $SO_4^=$ | <5 |
| TOC | 266 ppm |
| $Cl^-$ | 7200 ppm |
| Appearance | Clear - no flock present |

TABLE 3

| Vapor Space Analysis | |
|---|---|
| Compound | GC/MS Analysis |
| $H_2S$ | 4.5% |
| $CH_3OCH_3$ | 0.9% |
| $CH_3SH$ | 71.4% |
| $CH_3Br$ | 4.3% |
| $CH_3SCH_3$ | 15.7% |
| $CH_3S_2CH_3$ | ND* |

*ND = not detected

EXAMPLE 3

$H_2S$ Addition to Control Methyl Sulfide Byproduct

In this Example, the control of $CH_3SCH_3$ byproduct formation by the addition of $H_2S$ was studied. Stainless Steel bomb reactors were used in two reactions. In each run, the bomb was first cooled in and ice/acetone bath. Methyl bromide was then added to the bomb, followed by a NaSH solution. $H_2S$ was then added, and the bomb agitated by cylinder mixer. The maximum pressure was recorded, and the agitation stopped after 2.5 hours. The bomb was allowed to cool, and the final pressure recorded. The organic vapors were sampled into a gas bag and analyzed by GC/MS. The results are set forth in Table 2 below as run numbers 3—3 and 3—4. Run numbers 3—1 and 3—2 reported in Table 4 are from Examples 1 and 2 above, respectively.

TABLE 4

| | Run # | | | |
|---|---|---|---|---|
| | 3-1 | 3-2 | 3-3 | 3-4 |
| Bomb volume | 1000 ml | 100 ml | 300 ml | 300 ml |
| $CH_3Br$ | 234.0 g | 22.5 g | 48.6 g | 41.9 g |
| NaSH | 704.3 g | 66.3 g | 110.1 g | 97.2 g |
| $H_2S$ | | | | 14.2 g |
| $CH_3Br$/NaSH (molar ratio) | 0.196 | 0.200 | 0.260 | 0.241 |
| NaSH Composition | | | | |
| $Na_2CO_3$ | 4.15% | 1.9% | 1.9% | 1.9% |
| $NaHCO_3$ | | 3.0% | 3.0% | 3.0% |
| $Na_2S$ | 3.72% | ND | ND | ND |
| $H_2S$ | | 0.5% | 0.5% | 0.5% |
| NaSH | 20.2% | 27.9% | 27.9% | 27.9% |
| Specific Gravity | 1.189 g/ml | 1.189 g/ml | 1.189 g/ml | 1.189 g/ml |
| Maximum Pressure | — | — | 100 psig | 180 psig |
| Final Pressure | — | — | 50 psig | 50 psig |
| Product Analysis | | | | |
| $H_2S$ | 4.5% | 8.8% | 20% | 46.4% |

TABLE 4-continued

| | Run # | | | |
|---|---|---|---|---|
| | 3-1 | 3-2 | 3-3 | 3-4 |
| $CH_3OCH_3$ | 0.9% | 1.0% | 0.5% | 0.5% |
| $CH_3SH$ | 71.4% | 72.5% | 67.6% | 43.3% |
| $CH_3Br$ | 4.3% | 4.8% | 7.9% | ND |
| $CH_3SCH_3$ | 15.7% | 8.5% | 0.5% | ND |
| $CH_3S2CH_3$ | ND | 0.4% | 0.2% | ND |
| $CH_3S3CH_3$ | ND | ND | 0.1% | ND |

EXAMPLE 4

Packed Bed Reactor

A countercurrent continuous reactor was set up as in FIG. 1. $CH_3Br$ vapor flowed up and NaSH solution flowed down through the packed column. The column packing provided a large contact surface for vapor-liquid interaction. A series of runs were made with this countercurrent reactor. These reactions were vapor/liquid interactions since $CH_3Br$ vaporized and traveled up through the packed column while NaSH flowed down through the column. The NaSH feed contained 28% NaSH by weight, and the reaction temperature achieved was about 45° C. The results are set forth in Table 3 below. As demonstrated, the packed bed reactor can be effectively used to produce methyl mercaptan by a liquid/vapor contact process. Additionally, the use of NaSH in excess results in higher conversions of methyl bromide to methyl mercaptan.

TABLE 5

| Run | NaSH ml/min | $CH_3Br$ g/min | $H_2S$ ml/min | $CH_3SH$ Mole % | $CH_3Br$ Mole % | Percent Conversion |
|---|---|---|---|---|---|---|
| 1 | 3.9 | 1.0 | — | 5.83 | 94.17 | 5.83 |
| 2 | 7.8 | 1.0 | — | 33.26 | 66.74 | 33.26 |
| 3 | 7.8 | 1.0 | 90 | 41.33 | 58.67 | 41.33 |
| 4 | 9.9 | 1.0 | 90 | 63.04 | 39.96 | 63.04 |
| 5 | 12.7 | 1.0 | 90 | 70.95 | 29.05 | 70.95 |

EXAMPLE 5

Continuous Mixed, Pressurized Reactor

A continuous pressurized reactor system was set up as illustrated in FIG. 2. The pressurized continuous tube reactor was constructed from twelve 12" stainless steel static mixtures (0.25" O.D., 0.19" I.D.) with 26 mixing elements per individual mixer. These static mixers were connected with Swagelok fittings to withstand the reactor pressure (up to 250 psi). NaSH and methyl bromide were fed into the reactor using high pressure (280 psi max) positive displacement diaphragm pumps. $H_2S$ was fed into the reactor utilizing cylinder pressure. A stirred reactor was placed between the first and second static mixers to increase residence time and provide better mixing. Thermocouples were installed in the stirred reactor and at various points along the tube reactor. Pressure gauges with diaphragm seals were installed at the beginning and the end of the tube reactor. The tube reactor was connected to a surge pot with pressure relief valves to regulate pressure throughout the system. The reactant materials were pressured to a stainless steel vessel where vapor and liquid phases were separated. The liquid phase was drained and collected while the vapor phase is taken overhead to a large, stainless steel condenser with cooled outer jacket and inner cooling coil. The condenser was operated at approximately −20° C. The methyl mercaptan was collected in a stainless steel bomb while $H_2S$ was vented to a bleach scrubber. Crude $CH_3SH$ product was sampled between Column 35 and Column 39 (FIG. 2). Analyses were performed by Gas Chromatography. Final product analysis was also performed by Gas Chromatography and checked with GC/Mass Spectrometry. The feed conditions were as follows.

| Feed Conditions | |
|---|---|
| 28.6% wt/NaSH solution | 0.09 mol/min. |
| $CH_3Br$ liquid | 0.08 mol/min. |
| $H_2S$ gas | 0.025 mol/min. |

In several such runs, a slight excess of $H_2S$ enriched, 28% NaSH containing 1.8% sodium carbonate, moderate $H_2S$ flows, low pressure, and a reaction temperature of 75° C. were employed. A maximum conversion of methyl bromide to methyl mercaptan of 74% was achieved with average dimethyl sulfide concentrations in the product of 0.1%.

Several runs were then made using 20% NaSH to minimize $NaHCO_3$ precipitation problems. A maximum conversion of methyl bromide to $CH_3SH$ of 45% was achieved with an average dimethyl sulfide concentration of 0.1%.

Several additional runs were conducted using 28% NaSH. These runs were made wilt increased temperature (60° C.) and pressure (1.00 psi), A maximum conversion of methyl bromide to methyl mercaptan of 98.6% was achieved with dimethyl sulfide concentrations as low as 0.57%.

Several runs were then made with further increased pressure (210 psi). Maximum conversion of methyl bromide to methyl mercaptan of 99.5% was achieved with a dimethyl sulfide concentration of 0.18%.

A sustained 2.5 hour run using 28% NaSH was also conducted. The reactor temperature was 76° C. and the reactor pressure was maintained at 200 psig. Maximum conversion of methyl bromide to methyl mercaptan of >99.9% was achieved with dimethyl sulfide concentrations as low as 0.4%.

To avoid fouling of the system with precipitated sodium bicarbonate, a series of additional runs were made with dilute 20% NaSH. Reactor temperatures of 60° C. were obtained while maintaining a reactor pressure of 180 psi. Conversion of methyl bromide to methyl mercaptan ranged from 76.4% to 99.7% as a function of instantaneous methyl bromide/NaSH balance. Dimethyl sulfide concentrations ranged from 0.6% to nondetectable. Analysis of gas bag samples of the overhead to the scrubber found the contents to be 77% $H_2S$ with the remainder primarily methyl mercaptan. Fouling of the system from sodium bicarbonate precipitation was not seen and presented no problems during the 4 hour run.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A process for producing methyl mercaptan, comprising:
   stripping a geothermal brine containing bromide ions and hydrogen sulfide to remove the hydrogen sulfide as a gas;

contacting the hydrogen sulfide gas with an aqueous medium containing an alkali or alkaline earth metal hydroxide to form an aqueous medium containing an alkali or alkaline earth metal hydrosulfide;

intimately contacting and reacting the aqueous medium containing the alkali or alkaline earth metal hydrosulfide with methyl bromide in a reactor so as to form methyl mercaptan; and recovering the methyl mercaptan from the reactor.

2. The process of claim 1 wherein the aqueous medium is an aqueous solution of sodium hydrosulfide.

3. The process of clam 1 wherein the methyl bromide contains methyl ether and methanol as impurities.

4. The process of claim 2 wherein said reactor is operated at a pressure sufficient to maintain the methyl bromide in a liquid state.

5. The process of claim 4 which also comprises feeding hydrogen sulfide into the reactor to reduce the formation of dimethyl bromide as a byproduct, said pressure also being sufficient to maintain the hydrogen sulfide in a liquid state.

6. The process of claim 5 wherein said pressurized reactor is operated at a pressure of at least about 100 psig.

7. The process of claim 6 wherein the methyl bromide contains methyl ether and methanol as impurities.

8. The process of claim 2 wherein said reactor is a reactor containing solid material providing surface area promoting interaction of gaseous and liquid phases, and wherein said methyl bromide is in the gaseous state.

9. The process of claim 8 wherein the methyl bromide is fed as a gas to the reactor countercurrent to a feed of the aqueous sodium hydrosulfide solution.

10. The process of claim 8 which also comprises feeding hydrogen sulfide gas into the reactor to reduce the formation of dimethyl bromide as a byproduct.

11. The process of claim 1 wherein said reacting is conducted at a temperature of about 20° C. to about 150° C.

12. The process of claim 11 wherein said reacting is conducted at a temperature of about 20° C. to about 100° C.

13. A process for producing methyl mercaptan, comprising:

providing a reactor containing solid materials providing surface area for interaction among gas and liquid phases within the reactor;

feeding gaseous methyl bromide into the reactor;

contacting the gaseous methyl bromide in the reactor with an aqueous solution of sodium hydrosulfide, wherein said solid materials cause interaction among the gaseous methyl bromide and aqueous sodium hydrosulfide which react to form methyl mercaptan; and recovering the methyl mercaptan from the reactor.

14. The process of claim 13 wherein the methyl bromide contains methyl ether and methanol as impurities.

15. The process of claim 13 wherein the methyl bromide is fed as a gas to the reactor countercurrent to the feed of the aqueous sodium hydrosulfide solution.

16. The process of claim 15 which also comprises feeding hydrogen sulfide gas into the reactor to reduce the formation of dimethyl bromide as a byproduct.

17. The process of claim 16 wherein said reacting is conducted at a temperature of about 20° C. to about 100° C.

18. A process for producing methyl mercaptan, comprising:

continuously feeding methyl bromide through a pressurized, mixed reactor at a pressure sufficiently high to substantially maintain the methyl bromide in a liquid state;

continuously feeding an aqueous sodium hydrosulfide solution through the reactor simultaneously with the liquid methyl bromide, the mixed reactor mixing and reacting the methyl bromide and aqueous sodium hydrosulfide to form methyl mercaptan, and recovering the methyl mercaptan from the reactor.

19. The process of claim 18 wherein said pressurized reactor is operated at a pressure of at least about 100 psig.

20. The process of claim 18 wherein the methyl bromide contains methyl ether and methanol as impurities.

21. The process of claim 19 which also comprises feeding hydrogen sulfide into the reactor to reduce the formation of dimethyl bromide as a byproduct, said pressure also being sufficient to maintain the hydrogen sulfide in a liquid state.

22. The process of claim 18 wherein said reacting is conducted at a temperature of about 20° C. to about 150° C.

23. The process of claim 21 wherein said reacting is conducted at a temperature of about 20° C. to about 100° C.

24. The process of claim 22 wherein said reactor comprises a tubular reactor containing static mixing elements.

25. The process of claim 24 wherein the methyl bromide contains methyl ether and methanol as impurities.

* * * * *

UNITED STATES PATENT AND TRADEMARK OFFICE
CERTIFICATE OF CORRECTION

PATENT NO. : 5,481,042
DATED : January 2, 1996
INVENTOR(S) : John L. Burba, James T. Ayers, Preston E. Spires and John E. Hill It is certified that error appears in the above-identified patent and that said Letters Patent is hereby corrected as shown below:

In column 1, line 7, insert --to-- before "processes".

In column 3, line 30, please change "byproducts" to --byproduct--.

In column 5, line 23, please change "ho" to --to--.

In column 5, line 44, please change "ho" to --to--.

In column 10 line 28, please change "wilt" to --with--.

In column 10, line 29, please change "1.00" to --100--.

In column 10, line 29, please change the comma to a period.

In column 11, line 12, please change "clam" to --claim--.

Signed and Sealed this

Twenty-eighth Day of May, 1996

Attest:

BRUCE LEHMAN

Attesting Officer     Commissioner of Patents and Trademarks